(12) United States Patent
Anderson

(10) Patent No.: US 7,135,135 B2
(45) Date of Patent: Nov. 14, 2006

(54) SUPERABSORBENT WATER SENSITIVE MULTILAYER CONSTRUCTION

(75) Inventor: Stewart C. Anderson, Eden Prairie, MN (US)

(73) Assignee: H.B. Fuller Licensing & Financing, Inc., St. Paul, MN (US)

(*) Notice: Subject to any disclaimer, the term of this patent is extended or adjusted under 35 U.S.C. 154(b) by 279 days.

(21) Appl. No.: 10/121,171

(22) Filed: Apr. 11, 2002

(65) Prior Publication Data

US 2003/0194558 A1   Oct. 16, 2003

(51) Int. Cl.
- B29C 47/06 (2006.01)
- B29C 47/88 (2006.01)
- D01F 6/00 (2006.01)
- D02G 3/00 (2006.01)

(52) U.S. Cl. .................. 264/173.16; 264/211.14; 264/211.22; 264/184; 428/373; 428/411.1

(58) Field of Classification Search ............... 604/366, 604/367, 377; 442/394; 428/394, 402, 373, 428/411.1; 264/173.16, 211.14, 211.22, 264/184

See application file for complete search history.

(56) References Cited

U.S. PATENT DOCUMENTS

| | | |
|---|---|---|
| 4,090,013 A | 5/1978 | Ganslaw et al. |
| 4,335,722 A | 6/1982 | Jackson |
| 4,354,487 A | 10/1982 | Oczkowski et al. |
| 4,563,289 A | 1/1986 | Thompson |
| 4,702,944 A | 10/1987 | Thompson |
| 4,721,647 A | 1/1988 | Nakanishi et al. |
| 4,732,789 A | 3/1988 | Hauser et al. .......... 427/261 |
| 4,808,637 A | 2/1989 | Boardman et al. |
| 4,888,238 A | 12/1989 | Katz et al. |
| 4,914,170 A | 4/1990 | Chang et al. |
| 4,933,390 A | 6/1990 | Dabi et al. |
| 5,071,681 A | 12/1991 | Manning et al. |
| 5,075,344 A | 12/1991 | Johnson |
| 5,079,034 A | 1/1992 | Miyake et al. |
| 5,118,749 A | 6/1992 | Knutson .................. 524/460 |
| 5,122,544 A | 6/1992 | Bailey et al. |
| 5,126,382 A | 6/1992 | Hollenberg .............. 524/56 |
| 5,244,934 A | 9/1993 | Umeda et al. |
| 5,246,544 A | 9/1993 | Hollenberg et al. |
| 5,324,812 A * | 6/1994 | Speranza et al. .......... 528/338 |
| 5,487,736 A | 1/1996 | Van Phan |
| 5,489,469 A | 2/1996 | Kobayashi et al. |
| 5,547,747 A | 8/1996 | Trokhan et al. |
| 5,693,707 A | 12/1997 | Cheng et al. ............ 524/556 |
| 5,837,802 A | 11/1998 | Van Lith et al. |
| 5,849,837 A | 12/1998 | Wei et al. ............... 524/813 |
| 5,856,410 A | 1/1999 | Carrico et al. |
| 5,916,678 A | 6/1999 | Jackson et al. .......... 428/373 |
| 6,022,610 A | 2/2000 | Phan et al. |
| 6,051,317 A * | 4/2000 | Brueggemann et al. .... 428/378 |
| 6,103,317 A | 8/2000 | Asai et al. |
| 6,174,929 B1 | 1/2001 | Hahnle et al. |
| 6,284,367 B1 | 9/2001 | Gruhn et al. ............ 428/355 |
| 6,417,425 B1 | 7/2002 | Whitmore et al. |
| 6,426,445 B1 | 7/2002 | Young et al. |
| 6,495,080 B1 * | 12/2002 | Tsai et al. .............. 264/143 |
| 6,686,414 B1 * | 2/2004 | Anderson et al. ......... 524/556 |
| 6,843,874 B1 * | 1/2005 | Janssen .................. 156/230 |
| 2002/0090453 A1 * | 7/2002 | Muthiah et al. .......... 427/180 |
| 2002/0137837 A1 * | 9/2002 | Flautt et al. ............ 524/522 |

FOREIGN PATENT DOCUMENTS

| | | |
|---|---|---|
| EP | 702031 A2 | 3/1996 |
| EP | 708119 A1 | 4/1996 |
| EP | 0 781 538 A2 | 7/1997 |
| EP | 0 882 502 A1 | 12/1998 |
| GB | 2 191 779 A | 12/1987 |
| WO | WO 96/05234 | 2/1996 |
| WO | WO 01/74282 A1 | 10/2001 |

\* cited by examiner

*Primary Examiner*—Terrel Morris
*Assistant Examiner*—Lynda M. Salvatore

(57) ABSTRACT

A multilayer construction that includes a first layer that includes water sensitive thermoplastic polymer and a second layer disposed on the first layer, the second layer including superabsorbent polymer.

11 Claims, No Drawings

SUPERABSORBENT WATER SENSITIVE MULTILAYER CONSTRUCTION

BACKGROUND

The invention is directed to a superabsorbent multilayer construction.

Superabsorbent polymers, which are available as powders, particles, and aqueous compositions, absorb large quantities of water and are often used in absorbent articles to increase the absorbency of the article. Disposable diapers and feminine hygiene products often include superabsorbent polymers to enhance body fluid absorption. Superabsorbent polymers also have various applications in the medical, food, and agricultural industries.

SUMMARY

In one aspect, the invention features a multilayer construction that includes a first layer including water sensitive thermoplastic polymer, and a second layer disposed on the first layer, the second layer including superabsorbent polymer. In one embodiment, the thermoplastic polymer includes polyamide. In another embodiment the thermoplastic polymer includes the reaction product of polyoxyalkylene glycol diamine and an acid selected from the group consisting of dicarboxylic acid, dicarboxylic acid ester, and combinations thereof, the polyoxyalkylene glycol diamine having the formula $NH_2-(CH_2)_x-(OCH_2-CH_2)_y-O-(CH_2)_x-NH_2$, where $2 \leq X \leq 3$, and $1 \leq Y \leq 2$. In other embodiments, the thermoplastic polymer includes the reaction product of adipic acid and polyoxyalkylene glycol diamine. In another embodiment, the thermoplastic polymer is water soluble.

In some embodiments, the superabsorbent polymer includes crosslinked polyacrylate. In other embodiments, the superabsorbent polymer includes crosslinked and at least partially neutralized $\alpha,\beta$-beta ethylenically unsaturated monomers selected from the group consisting of monocarboxylic acid monomers, dicarboxylic acid monomers, acid anhydride monomers, and combinations thereof.

In one embodiment, the construction exhibits an absorption rate greater than the absorption rate of the superabsorbent polymer layer in the absence of the thermoplastic layer.

In other embodiments, an above-described multilayer construction is a film. In one embodiment the film exhibits an absorption rate greater than the absorption rate of the superabsorbent polymer layer in the absence of the thermoplastic layer. In some embodiments, the film is flexible.

In some embodiments, an above-described multilayer construction is a fiber.

In another aspect, the invention features an article that includes a nonwoven web and an above-described multilayer construction disposed on the web.

In some aspects, the invention features a multi-component fiber that includes a first component that includes water sensitive thermoplastic polymer, and a second component that includes superabsorbent polymer, the second component being disposed on the first component. In one embodiment, the first component includes a core and the second component includes a sheath.

In other aspects the invention features a multi-component yarn that includes a first component that includes water sensitive thermoplastic polymer, and a second component comprising superabsorbent polymer, the second component being disposed on the first component. In some embodiments, the first component includes a core that includes the water sensitive thermoplastic polymer. In another embodiment, the second component includes a sheath that includes the superabsorbent polymer.

In another embodiment, a disposable article (e.g., a diaper) includes an above-described multilayer construction.

In another aspect, the invention features a method of making a multilayer construction that includes coating an aqueous water soluble superabsorbent polymer composition on a water sensitive thermoplastic film.

In one embodiment, the method includes providing a molten water sensitive thermoplastic polymer, and contacting the molten thermoplastic polymer with an aqueous water soluble superabsorbent polymer composition. In another embodiment, the molten thermoplastic polymer is in a form selected from the group consisting of fibers, filaments and combinations thereof. In some embodiments, the molten thermoplastic polymer is in the form of a film.

The invention features a superabsorbent self-supporting film that is capable of degrading in water, is flushable, and degrades in a sewer system. The multiplayer construction and can also be constructed to include a water soluble thermoplastic polymer layer and be capable of dissolving in water. The invention also features a multilayer construction that can be disposed on a substrate or incorporated into an article to render the article water soluble, water swellable, water dispersible or a combination thereof.

The multilayer construction is well suited to use in personal hygiene products and can be incorporated into such products to render the products more able to degrade in sewer and waste disposal systems.

The multilayer construction can be constructed to be thermally bonded to a substrate.

The multilayer construction, when in the form of a continuous or discontinuous film can allow liquid to pass through the layers of the construction to a second layer, e.g., an absorbent core, where it can then be stored. Storage of the liquid in the second layer allows the liquid to be maintained away from the skin of the user.

GLOSSARY

In reference to the invention, these terms have the meanings set forth below:

"Water sensitive" means water soluble, water dispersible, water swellable, and combinations thereof.

Other features and advantages will be apparent from the following description of the preferred embodiments and from the claims.

DETAILED DESCRIPTION

The multilayer construction (e.g., film) includes a layer of superabsorbent polymer disposed on a layer of water sensitive thermoplastic polymer. When the superabsorbent layer of the multilayer construction is contacted with an aqueous composition it forms a gel and the thermoplastic layer at the interface with the gelling superabsorbent layer substantially maintains its integrity as the superabsorbent layer gels. The multilayer construction can be constructed to gel at a rate faster than the gel rate that would be exhibited by the superabsorbent polymer layer in the absence of the water sensitive thermoplastic layer.

The superabsorbent layer includes superabsorbent polymer preferably in the form of a continuous or discontinuous coating or film. The superabsorbent polymer absorbs many times its own weight in water, preferably at least 50 times, more preferably at least 100 times, most preferably at least 150 times its weight in water. The ability of the superabsorbent polymer to absorb water is related to the degree of crosslinking present in the superabsorbent polymer. Increasing the degree of crosslinking increases the superabsorbent polymer's total fluid holding capacity under load. The degree of crosslinking is preferably optimized to obtain a composition in which the rate and amount of absorbency are optimized. Preferred superabsorbent polymers are at least 10%, more preferably from about 10% to about 50%, most preferably from about 20% to 40% crosslinked. Examples of suitable superabsorbent polymers include crosslinked and polymerized α,β-beta ethylenically unsaturated mono- and dicarboxylic acids and acid anhydride monomers including, e.g., acrylic acid, methacrylic acid, crotonic acid, maleic acid/anhydride, itaconic acid, fumaric acid, and combinations thereof.

The superabsorbent layer is preferably formed from an aqueous composition of water soluble superabsorbent polymer (i.e., a polymer that exhibits superabsorbent properties when crosslinked), and crosslinking agent. The aqueous superabsorbent polymer composition exhibits a pH of from about 7 to about 10, preferably a pH greater than 7, which can be achieved by adding a pH adjusting agent (e.g., a base) to the aqueous superabsorbent polymer composition. Examples of useful pH adjusting agents include alkali metal hydroxide (e.g., sodium hydroxide and potassium hydroxide), alkali metal alkoxide, alkaline earth metal hydroxide (e.g., calcium hydroxide), and combinations thereof. The pH adjusting agent assists in neutralizing the acid groups of the water soluble superabsorbent polymer. Preferably alkali metal hydroxide or alkaline earth metal hydroxide is added to neutralize from about 50% to about 95% of the carboxyl groups, preferably from greater than 65% to about 95% of the carboxyl groups, more preferably from about 70% to about 95% of the carboxyl groups, more preferably from about 70% to about 85% of the carboxyl groups, most preferably about 75% of the carboxyl groups. The water soluble superabsorbent polymer is then further neutralized (e.g., at least 100% neutralized) with a volatile base. The volatile base dissipates from the aqueous water soluble superabsorbent polymer composition as the composition dries, which allows the crosslinking agent to crosslink the water soluble superabsorbent polymer to form a high molecular weight polymer, i.e., the superabsorbent polymer. Examples of suitable volatile bases include ammonia, e.g., ammonium hydroxide, amines including, e.g., methylamine and dimethylamine, and combinations thereof.

The viscosity of the aqueous water soluble superabsorbent polymer composition is selected to facilitate application of the composition on a substrate (e.g., the water soluble thermoplastic polymer component). Useful aqueous water soluble superabsorbent polymer compositions have a viscosity of from about 50 cPs to about 50,000 cPs, more preferably, in increasing order of preference, from about 100 cPs to about 30,000 cPs, from abut 100 cPs to about 20,000 cPs, from about 100 cPs to abut 10,000 cPs, from about 100 cPs to about 5000 cPs, from about 100 cPs to about 2500 cPs at room temperature (i.e., 25° C.) for a 20% by weight solids composition. Preferably the water soluble superabsorbent polymer has a molecular weight of from about 9000 Mw to about 4,000,000 Mw, more preferably from about 20,000 Mw to about 1,000,000 Mw, most preferably from about 100,000 Mw to about 200,000 Mw.

The aqueous water soluble superabsorbent polymer composition includes from 5% by weight to about 65% by weight, preferably from about 10% by weight to about 50% by weight, more preferably from about 20% by weight to about 40% by weight solids.

The crosslinking agent is selected to complex with the functional hydrophilic groups of the water soluble superabsorbent polymer. Preferred crosslinking agents complex with the functional groups on the water soluble superabsorbent polymer once the water phase of the polymer composition has dissipated. Useful crosslinking agents include, e.g., di- and trivalent crosslinking salts including, e.g., zirconium salts, zinc salts, chromium salts, and combinations thereof, zirconium ions, which can be mixed with ferric aluminum ions, chromic ions, titanium ions, and aziridine, and combinations thereof. Other useful crosslinking agents are described in U.S. Pat. No. 4,090,013 and incorporated herein. Useful commercially available crosslinking agents include ammonium zirconyl carbonate available under the trade designations BACOTE 20 and ZIRMEL 1000 from Magnesium Elektron, Inc. (Flemington, N.J.), and aziridine crosslinking agents available under the trade designation NEOCRYL CX-100 from Zeneca Resins (Wilmington, Me.). Preferably the crosslinking agent is added to the aqueous superabsorbent prepolymer composition in an amount of from about 2 parts to about 10 parts, preferably from about 2 parts to about 8 parts, most preferably from about 4 parts to 6 parts.

The crosslinking agent can also be provided separately from the aqueous water soluble superabsorbent polymer composition. In some applications, the aqueous water soluble superabsorbent polymer composition is applied to the water sensitive thermoplastic layer prior to or after application of the crosslinking agent in a two-step process. When the aqueous water soluble superabsorbent polymer and crosslinking agent are applied separately, the aqueous water soluble superabsorbent polymer composition is preferably dried prior to contact with the crosslinking agent.

Preferred superabsorbent polymers are capable of being hydroplasticized by ambient moisture. The hydroplasticized superabsorbent polymer provides a pliant film exhibiting extensibility and flexibility. Preferably the superabsorbent polymer absorbs moisture from the air at ambient temperature and 50% relative humidity in an amount of at least about 5% by weight, more preferably at least about 10% by weight, most preferably at least about 20% by weight of the anhydrous superabsorbent polymer.

The aqueous water soluble superabsorbent polymer composition may also include small amounts of water soluble monomers including, e.g., 2-hydroxyethyl acrylate, 2-hydroxyethyl methacrylate, vinyl pyrrolidone, acrylamide, methacrylamide, sodium vinyl sulfonated, and 1-allyloxy-2-hydroxypropane sulfonate.

Useful water sensitive thermoplastic polymers include water soluble thermoplastic polymers, water dispersible thermoplastic polymers and water swellable thermoplastic polymers. Suitable water sensitive thermoplastic polymers include crystalline water sensitive thermoplastic polymers and amorphous water sensitive thermoplastic polymers. The term "crystalline polymer" means those polymers that retain their rubbery elastomeric or flexible properties above the glass transition, until the melting temperature has been surpassed. Melting of the crystalline polymer is also accompanied by a loss of crystalline X-ray diffraction effects. An "amorphous polymer" is a polymer that, with increasing temperature, passes from a solid phase to a liquid phase without a discernible transition point.

Suitable water soluble crystalline thermoplastic polymers include the reaction product of a polyoxyalkylene glycol diamine or a polyoxyalkylene glycol amine, and a dicarboxylic acid or dicarboxylic acid ester. Preferred polyoxyalkylene glycol diamines have the formula:

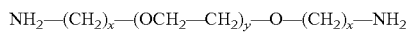

$NH_2-(CH_2)_x-(OCH_2-CH_2)_y-O-(CH_2)_x-NH_2$ where $2 \leq X \leq 3$, and $1 \leq Y \leq 2$. Examples of suitable polyoxyalkylene glycol diamines include triethylene glycol diamine, wherein X=2 and Y=1, and tetraethylene glycol diamine, wherein $2 \leq X \leq 3$ and Y=2. Useful commercially available polyoxyalkylene glycol diamines are available under the trade designations JEFFAMINE XTJ-504 and JEFFAMINE EDR-192 (tetraethylene glycol diamine) from Huntsman Chemical Co. (Houston, Tex.). A preferred diamine is 4,7,10-trioxatridecane-1,13-diamine (TTD diamine) where X=3 and Y=2, which is available from BASF (Parsippany, N.J.).

Useful polyoxyalkylene glycol amines include JEFFAMINE D-230, D-400, XTJ-500, XTJ-501, and XTJ-502 provided a chain terminator acid or amine is employed during the reaction, and/or additional ingredients such as waxes, tackifiers, crystalline polymers, and monoacids are subsequently combined with the reacted polyamide When adipic acid is reacted with trioxytridecane-1,13-diamine and JEFFAMINE D-230, for example, the resulting polyamide is relatively slow setting relative to the reaction of adipic acid and trioxytridecane-1,13-diamine alone. The polyoxyalkylene glycol diamine is reacted with an equal stoichiometric ratio of a dicarboxylic acid.

Suitable dicarboxylic acids include those dicarboxylic acids having from 5 to 36 carbon atoms including, e.g., adipic acid, pimelic acid, azelaic acid, sebacic acid, suberic acid, dodecanedioic acid, terephthalic acid, isophthalic acid, t-butyl isophthalic acid, dimer acid, and mixtures thereof. The esters and anhydrides of these acids may also be used.

Particularly useful water soluble polyether amides have a melting point no greater than 190° C. and include, e.g., the reaction products of adipic acid and JEFFAMINE XTJ-504, adipic acid and JEFFAMINE EDR-192, and adipic acid and TTD diamine.

Suitable crystalline water soluble polyamides are commercially available under the trade designations NP-2126, NP-2110, NP-2116, and NP-2068 from H. B. Fuller Company (St. Paul, Minn.).

Suitable crystalline water dispersible polymers include, e.g., polyethylene oxide available, e.g., from Union Carbide (Danbury, Conn.) and crystalline polyesters.

Suitable amorphous water sensitive thermoplastic polymers include, e.g., polyvinyl alcohol, polyvinyl pyrrolidone, polyvinyl pyrrolidone/vinyl acetate, polyvinyl pyrrolidone/acrylic acid, polyetheroxazoline, and linear and branched water dispersible polyesters.

Suitable commercially available amorphous water dispersible thermoplastic polymers include, e.g., polyvinyl alcohol available under the trade designations GROHSERAN L-301 and GROHSERAN L-302 from Nippon Groshei (Japan), and under the trade designation UNITIKA from Unitaka Ltd. (Japan); polyvinyl pyrrolidone available from BASF (Mount Olive, N.J.), and International Specialty Products (Wayne, N.J.); polyvinyl pyrrolidone/vinyl acetate copolymer and polyvinyl pyrrolidone/acrylic acid available under the trade designation ACRYLIDONE, both of which are available from ISP; polyethyloxazoline available under the trade designation PEOX from The Dow Chemical Company (Freeport, Tex.), and under the trade designation AQUAZOL from PCI Incorporated (Tucson, Ariz.), polyvinyl methyl ether available under the trade designation AMO-BOND from Amoco Chemical Co., linear polyesters, polyacrylamide, and water dispersible polyesters and copolyesters available under the trade designation EASTMAN AQ including EASTMAN AQ-14000, EASTMAN AQ-1950, and EASTMAN AQ-1045 from Eastman Chemical Company (Kingsport, Tenn.).

Suitable water dispersible polyesters and copolyesters are available under the EASTMAN AQ trade designation and include linear polyesters or branched sulfonated copolyesters. Such polymers are saline and body fluid insoluble, yet dispersible in tap water. The Tg of the branched water dispersible copolyesters ranges from about −5° C. to 7° C., whereas the linear polyesters have a Tg from about 30° C. to about 60° C. Linear thermoplastic water dispersible polyesters are commercially available under the EASTMAN AQ series of trade designations including, e.g., EASTMAN AQ 35S (7,000 Mn), AQ 38S (10,000 Mw), and AQ 55S (8,000 Mn) all from Eastman Chemical Company (Kingsport, Tenn.). Branched thermoplastic water dispersible polyesters are commercially available under the EASTMAN AQ series of trade designations including, e.g., EASTMAN AQ 1045, AQ 1350, AQ 1950, and AQ 14000 from Eastman Chemical Company.

Other useful water sensitive polymers are commercially available under the Hydromelt trade designation from H. B. Fuller Company (St. Paul, Minn.) and include NP 2116, NP 2055, NP 2068, and NP 2110.

Useful water sensitive thermoplastic polymers and their methods of manufacture are disclosed, e.g., in U.S. Pat. Nos. 3,882,090 (Fagerberg et al.), 5,053,484 (Speranza et al.), 5,118,785 (Speranza et al.), 5,086,162 (Speranza et al.), 5,324,812 (Speranza et al.), 5,899,675 (Ahmed et al.), 5,863,979 (Ahmed et al.), 5,663,286 (Ahmed et al.), and 5,869,596 (Ahmed et al.), and incorporated herein.

The water soluble thermoplastic polymer layer can also include additives including, e.g., waxes, tackifying resins, crystalline polymers, monocarboxylic acids, and mixtures thereof as well as monocarboxylic acids and monoamines.

Preferably the multilayer construction is oriented such that the superabsorbent polymer layer is exposed to a fluid to be absorbed, e.g., water, body fluid, and combinations thereof.

The multilayer construction can exist in a variety of forms including, e.g., fibers (e.g., a multicomponent fiber, e.g., core-sheath construction), yarn (e.g., multicomponent yarn), film (e.g., a freestanding film), a coating on a substrate (including, e.g., woven and nonwoven substrates, porous substrates, films, fibers, and yarns), and combinations thereof. The multilayer construction, itself, as well as the layers of the multilayer construction can be continuous or discontinuous including, e.g., striped, dotted, and patterned.

The multilayer construction can be free standing (e.g., a film, fiber, and yarn) or associated with, e.g., disposed on, a substrate including, e.g., fibers, yarns, webs (woven and nonwoven), films, release liners, and combinations thereof. Useful fibers include cellulose fibers including, e.g., wood pulp, cotton, silk, and wool, and synthetic fibers including, e.g., nylon, rayon, polyesters, acrylics, polypropylenes, polyethylene, polyvinyl chloride, polyurethane, glass, and combinations thereof. The multilayer construction can be disposed on the substrate in various forms including, e.g., continuous and discontinuous (e.g., striped, dotted, and patterned) coatings, laminates, and combinations thereof.

The layers of the construction can be applied to or formed on the substrate simultaneously or sequentially using a variety of techniques including, e.g., immersing, soaking, impregnating, spraying, extruding (e.g., coextrusion), laminating, coating (e.g., dip coating, slot, gravure, knife, and contact coating), and combinations thereof. Porous substrates, for example, can be sequentially impregnated with the aqueous superabsorbent polymer and the water sensitive thermoplastic polymer.

Preferably the aqueous water soluble superabsorbent polymer composition is applied to the water sensitive component of the construction while the water sensitive thermoplastic component is at a higher temperature, e.g., in a molten state or a temperature in the melt temperature range of the water sensitive thermoplastic polymer, relative to the aqueous superabsorbent polymer composition. In the case where the water sensitive component is formed by extrusion, for example, the aqueous water soluble superabsorbent polymer composition can be applied to the water sensitive component as it is extruded, and, in the case of fibers and filaments, the aqueous water soluble superabsorbent polymer composition can be applied to the fibers or filaments at or near the point at which the fibers or filaments are released from the fiber or filament forming orifice. The relatively higher temperature exhibited by the water sensitive thermoplastic component as it is extruded from an orifice increases the rate of dissipation of the aqueous component of the aqueous water soluble superabsorbent polymer composition applied thereto.

The multilayer construction is suitable for use in a variety of articles including, e.g., absorbent articles such as diapers, sanitary napkins, bandages, wound care products, surgical pads, drapes, and gowns as well as various paper products such as paper towels, toilet paper, and facial tissue, cable wrap, and packaging.

One useful article includes a fibrous nonwoven web and the multilayer construction disposed on the web. The multilayer construction can include perforations to allow liquid to pass through the construction to a second layer, e.g., a nonwoven web.

The multilayer construction also can be incorporated into an absorbent article that includes, e.g., a body fluid pervious top sheet, an acquisition layer, an absorbent layer (e.g., a fibrous core), a body fluid impermeable back sheet, and combinations thereof. The acquisition layer preferably is capable of dispersing liquid to the surface of the absorbent layer. The absorbent layer may include loose fibers, fibers held together through a binder, compressed fibers, and combinations thereof. The fibers of the absorbent layer may be natural fibers (e.g., wood pulp, jute, cotton, silk, and wool, and combinations thereof), synthetic fibers including (e.g., nylon, rayon polyester, acrylics, polypropylenes, polyethylene, polyvinyl chloride, polyurethane, and combinations thereof), and combinations thereof. The multilayer construction can be in the form of a layer disposed between any of the components.

In one absorbent article, the multilayer construction is perforated and disposed between the wearer of the absorbent article and an absorbent layer such that the thermoplastic layer is the first layer of the multilayer construction that is available for contact with a liquid. The perforations allow a liquid to pass through the multilayer construction from the thermoplastic layer to the superabsorbent layer. The superabsorbent layer then gels upon contact with the water and the absorbent layer of the absorbent article absorbs the water.

The invention will now be described by way of the following examples. All ratios and percentages are by weight unless otherwise indicated.

EXAMPLES

Example

FULATEX PD8081H aqueous polyacrylic acid solution polymer and ammonium zirconyl carbonate composition (H. B. Fuller Company, St. Paul, Minn.) was coated onto a 50 um thick NP 2116 polyamide film (H. B. Fuller Company) and dried to form a film construction that included a 15 um superabsorbent polymer coating on the 50 um polyamide film.

Water droplets were dropped onto the superabsorbent polymer surface of the film construction using an eye dropper. The treated film was observed. The water was rapidly adsorbed and then absorbed by the superabsorbent polymer and formed a gel in five seconds. The water was then absorbed by the thermoplastic layer of the film construction. After three minutes the film construction had dissolved in the location of the water droplets.

Other features are present in the claims.

What is claimed is:

1. A method of making a multilayer article comprising:
   providing a molten water sensitive thermoplastic polymer; and
   contacting said molten thermoplastic polymer with an aqueous composition of a water soluble superabsorbent polymer.

2. The method of claim 1, wherein said multilayer article is in a form selected from the group consisting of fibers, filaments and combinations thereof.

3. The method of claim 1, wherein said multilayer article is in the form of a film.

4. The method of claim 1, wherein said superabsorbent polymer composition is contacted to said water sensitive thermoplastic polymer while said water sensitive thermoplastic polymer is at a higher temperature than that of said superabsorbent polymer composition.

5. The method of claim 4, wherein said water sensitive thermoplastic composition is formed by extrusion.

6. The method of claim 5, wherein said superabsorbent polymer composition is applied to said water sensitive thermoplastic composition as said water sensitive thermoplastic composition is extruded.

7. The method of claim 4, comprising the further step of crosslinking said superabsorbent polymer composition.

8. The method of claim 1, comprising the further step of including a crosslinked polyacrylate in said superabsorbent polymer.

9. The method of claim 1, comprising the further step of including a crosslinked and at least partially neutralized $\alpha,\beta$-ethylenically unsaturated monomer selected from the group consisting of monocarboxylic acid monomers, dicarboxylic monomers, acid anhydride monomers, and combinations thereof in the superabsorbent polymer.

10. The method of claim 1, comprising the further step of including as the thermoplastic polymer, the reaction product of (a) a polyoxyalkylene glycol diamine having the formula $NH_2$—$(CH_2)_x$—$(OCH_2$—$CH_2)_y$—$O$—$(CH_2)_x$—$NH_2$, wherein $2 \leq X \leq 3$ and $1 \leq Y \leq 2$, and (b) and an acid selected from the group consisting of dicarboxylic acid, dicarboxylic acid ester, and combinations thereof.

11. The method of claim 1, comprising the further step of including as the thermoplastic polymer, the reaction product of adipic acid and polyoxyalkylene glycol diamine.

* * * * *